United States Patent
Horkheimer et al.

(10) Patent No.: US 9,671,362 B2
(45) Date of Patent: Jun. 6, 2017

(54) PH SENSOR WITH BONDING AGENT DISPOSED IN A PATTERN

(71) Applicant: Honeywell International Inc., Morristown, NJ (US)

(72) Inventors: Donald Horkheimer, Minneapolis, MN (US); Paul S. Fechner, Plymouth, MN (US); David S. Willits, Long Lake, MN (US)

(73) Assignee: Honeywell International Inc., Morris Plains, NJ (US)

( * ) Notice: Subject to any disclaimer, the term of this patent is extended or adjusted under 35 U.S.C. 154(b) by 258 days.

(21) Appl. No.: 13/952,879

(22) Filed: Jul. 29, 2013

(65) Prior Publication Data

US 2015/0028395 A1    Jan. 29, 2015

(51) Int. Cl.
| | |
|---|---|
| *G01N 27/333* | (2006.01) |
| *G01N 27/414* | (2006.01) |
| *B32B 37/12* | (2006.01) |
| *C03C 27/00* | (2006.01) |
| *H01L 23/00* | (2006.01) |

(52) U.S. Cl.
CPC ....... *G01N 27/414* (2013.01); *B32B 37/1292* (2013.01); *C03C 27/00* (2013.01); *G01N 27/4148* (2013.01); *H01L 24/33* (2013.01); *H01L 24/83* (2013.01); *H01L 2924/01322* (2013.01); *H01L 2924/12042* (2013.01); *H01L 2924/35* (2013.01)

(58) Field of Classification Search
None
See application file for complete search history.

(56) References Cited

U.S. PATENT DOCUMENTS

| | | | |
|---|---|---|---|
| 4,505,799 A | 3/1985 | Baxter | |
| 8,186,226 B2 | 5/2012 | Ricks | |
| 8,402,835 B2 | 3/2013 | August et al. | |
| 8,608,896 B2 * | 12/2013 | Horstkemper | B29C 65/5021 156/295 |

(Continued)

FOREIGN PATENT DOCUMENTS

| | | |
|---|---|---|
| DE | 19814857 | 10/1999 |
| DE | 102008040187 | 1/2010 |

(Continued)

OTHER PUBLICATIONS

European Patent Office, "Office Action for Application No. 14167596.7", "for Foreign Counterpart to U.S. Appl. No. 13/952,888", Dec. 8, 2014, pp. 1-10, Published in: EP.

(Continued)

*Primary Examiner* — Ali Naraghi
(74) *Attorney, Agent, or Firm* — Fogg & Powers LLC

(57) ABSTRACT

Embodiments described herein provide for a pH sensor that comprises a substrate and an ion sensitive field effect transistor (ISFET) die. The ISFET die includes an ion sensing part that is configured to be exposed to a medium such that it outputs a signal related to the pH level of the medium. The ISFET die is bonded to the substrate with at least one composition of bonding agent material disposed between the ISFET die and the substrate. One or more strips of the at least one composition of bonding agent material is disposed between the substrate and the ISFET die in a first pattern.

14 Claims, 13 Drawing Sheets

(56) References Cited

U.S. PATENT DOCUMENTS

| | | | | |
|---|---|---|---|---|
| 2005/0017256 | A1* | 1/2005 | Slater, Jr. | H01L 33/40 257/94 |
| 2007/0215985 | A1* | 9/2007 | Chen | H01L 23/42 257/622 |
| 2008/0250847 | A1 | 10/2008 | Kitani et al. | |
| 2009/0120490 | A1* | 5/2009 | Huang | C03C 3/068 136/252 |
| 2010/0140089 | A1 | 6/2010 | Chou et al. | |
| 2012/0273845 | A1* | 11/2012 | Brown | G01N 27/414 257/253 |
| 2013/0164466 | A1 | 6/2013 | Khadilkar et al. | |
| 2015/0028396 | A1 | 1/2015 | Horkheimer et al. | |

FOREIGN PATENT DOCUMENTS

| | | |
|---|---|---|
| EP | 2518483 | 10/2012 |
| JP | H10227759 | 8/1998 |

OTHER PUBLICATIONS

Kyo et al., "Trial of Hydrothermal Plume Sensing Using Newly Developed ISFET pH Sensor", "IEEE Proceedings: Celebrating the Past, Temaing Toward the Future", Sep. 22, 2003, pp. 1732-1737, Publisher: IEEE, Published in: San Diego, CA.

Venkatesan et al., "Study on Behavior of Carbon Fiber-Reinforced Composite for Deep Sea Applications", "2002 Offshore Technology Conference", May 9, 2002, pp. 1-9, Published in: Houston, TX.

U.S. Patent and Trademark Office, "Office Action", "from U.S. Appl. No. 13/952,888", May 27, 2015, pp. 1-28, Published in: US.

Sverdlov, "Chapter 2: Scaling, Power Consumption, and Mobility Enhancement Techniques", "Strain-Induced Effects in Advanced MOSFETs; at least as early as Dec. 2011", 2011, pp. 5-22, Publisher: Springer-Verlag.

Arghavani et al., "A Reliable and Manufacturable Method to Induce a Stress of >1 GPa on a P-Channel MOSFET in High Volume Manufacturing", "IEEE Electron Device Letters", Feb. 2006, pp. 114-116, vol. 27, No. 2.

Barlian et al., "Review: Semiconductor Piezoresistance for Microsystems", "Proceedings of the IEEE", Apr. 1, 2009, pp. 513-552, vol. 97, No. 3, Publisher: IEEE.

Chang et al., "Piezoresistive Sensor of Short-and Long-Channel MOSFETs on (100) Silicon", Dec. 19, 2008, pp. 1-4, Publisher: IEEE.

Hopcroft et al., "What is the Young's Modulus of Silicon", "Journal of Microelectromechanical Systems", Apr. 2010, pp. 229-238, vol. 19, No. 2.

Sun et al., "Strain Effect in Semiconductors", "at least as early as Dec. 2010", 2010, pp. 1-10, Publisher: Springer Science + Business Media, LLC.

Thompson et al., "Uniaxial-Process-Induced Strained-Si: Extending the CMOS Roadmap", "IEEE Transactions on Electron Devices", May 2006, pp. 1010-1020, vol. 53, No. 5.

Thompson et al., "Future of Strained Si/Semiconductors in Nanoscale MOSFETs", Sep. 2006, pp. 1-4, Publisher: University of Florida.

Song et al., "Development of In-situ Laser Vacuum Annealing and Sealing Processes for an Application to Field Emission Displays", "Vacuum Microelectronics Conference, 2001. IVMC 2001. Proceedings of the 14th International", Aug. 2001, pp. 219-220.

Wu et al., "Glass Frit as a Hermetic Joining Layer in Laser Based Joining of Miniature Devices", "IEEE Transactions on Components and Packaging Technologies", Jun. 2010, pp. 470-477, vol. 33, No. 2.

U.S. Patent and Trademark Office, "Restriction Requirement", "from U.S. Appl. No. 13/952,888", Sep. 4, 2014, pp. 1-7, Published in: US.

European Patent Office, "European Search Report for Application No. 14167601.5", "from Foreign Counterpart to U.S. Appl. No. 13/952,879", Oct. 22, 2014, pp. 1-10, Published in: EP.

Martz et al., "Testing the Honeywell Durafet for Seawater pH Applications", Jan. 1, 2010, pp. 172-184, Publisher: American Society of Limnology and Oceanography, Inc.

U.S. Patent and Trademark Office, "Advisory Action", "U.S. Appl. No. 13/952,888", Feb. 9, 2016, pp. 1-5.

U.S. Patent and Trademark Office, "Final Office Action", "from U.S. Appl. No. 13/952,888", Nov. 25, 2015, pp. 1-23, Published in: US.

U.S. Patent and Trademark Office, "Notice of Allowance", "U.S. Appl. No. 13/952,888", Jul. 7, 2016, pp. 1-22, Published in: US.

European Patent Office, "Communication under Rule 71(3) EPC from EP Application No. 14167596.7 mailed Aug. 5, 2016", "from Foreign Counterpart of U.S. Appl. No. 13/952,888", Aug. 5, 2016, pp. 1-40, Published in: EP.

United States Patent and Trademark Office, "Notice of Allowance", "from U.S. Appl. No. 13/952,888", Oct. 21, 2016, pp. 1-11, Published in: US.

* cited by examiner $$\phi \cong \underbrace{[\pi_1][\sigma_1]}_{\text{State 1}} - \underbrace{[\pi_2][\sigma_2]}_{\text{State 2}}$$

FIG. 11

PH SENSOR WITH BONDING AGENT DISPOSED IN A PATTERN

STATEMENT REGARDING FEDERALLY SPONSORED RESEARCH OR DEVELOPMENT

This invention was made with Government support under contract number N00014-10-1-0206 awarded by Office of Naval Research. The Government has certain rights in the invention.

BACKGROUND

Researchers use sensor devices to measure pH levels in the ocean. pH levels in the ocean are related to the amount of CO2 dissolved in the ocean. By measuring the pH levels in the ocean at various depths, researchers may be able to monitor Global Warming risks and ocean health. Some pH sensors are capable of measuring these levels by immersing ion sensitive field effect transistors (ISFETs) into the ocean. In the oceans, there is an inverse relationship between water temperature and pressure. Near the surface, temperatures are high and pressures are low. In deep sea, temperatures are lower but pressure is high. Such wide pressure variation can limit conventional pH sensor accuracy because of the measurement errors induced by large mechanical stresses associated in deep seas.

SUMMARY

Embodiments described herein provide for a pH sensor that comprises a substrate and an ion sensitive field effect transistor (ISFET) die. The ISFET die includes an ion sensing part that is configured to be exposed to a medium such that it outputs a signal related to the pH level of the medium. The ISFET die is bonded to the substrate with at least one composition of bonding agent material disposed between the ISFET die and the substrate. One or more strips of the at least one composition of bonding agent material is disposed between the substrate and the ISFET die in a first pattern.

DRAWINGS

FIG. 11 is an example of a mathematical model of an effect achieved by the pH sensor of FIG. 1.

In accordance with common practice, the various described features are not drawn to scale but are drawn to emphasize features relevant to the present description. Reference characters denote like elements throughout figures and text.

DETAILED DESCRIPTION

Figure 1:
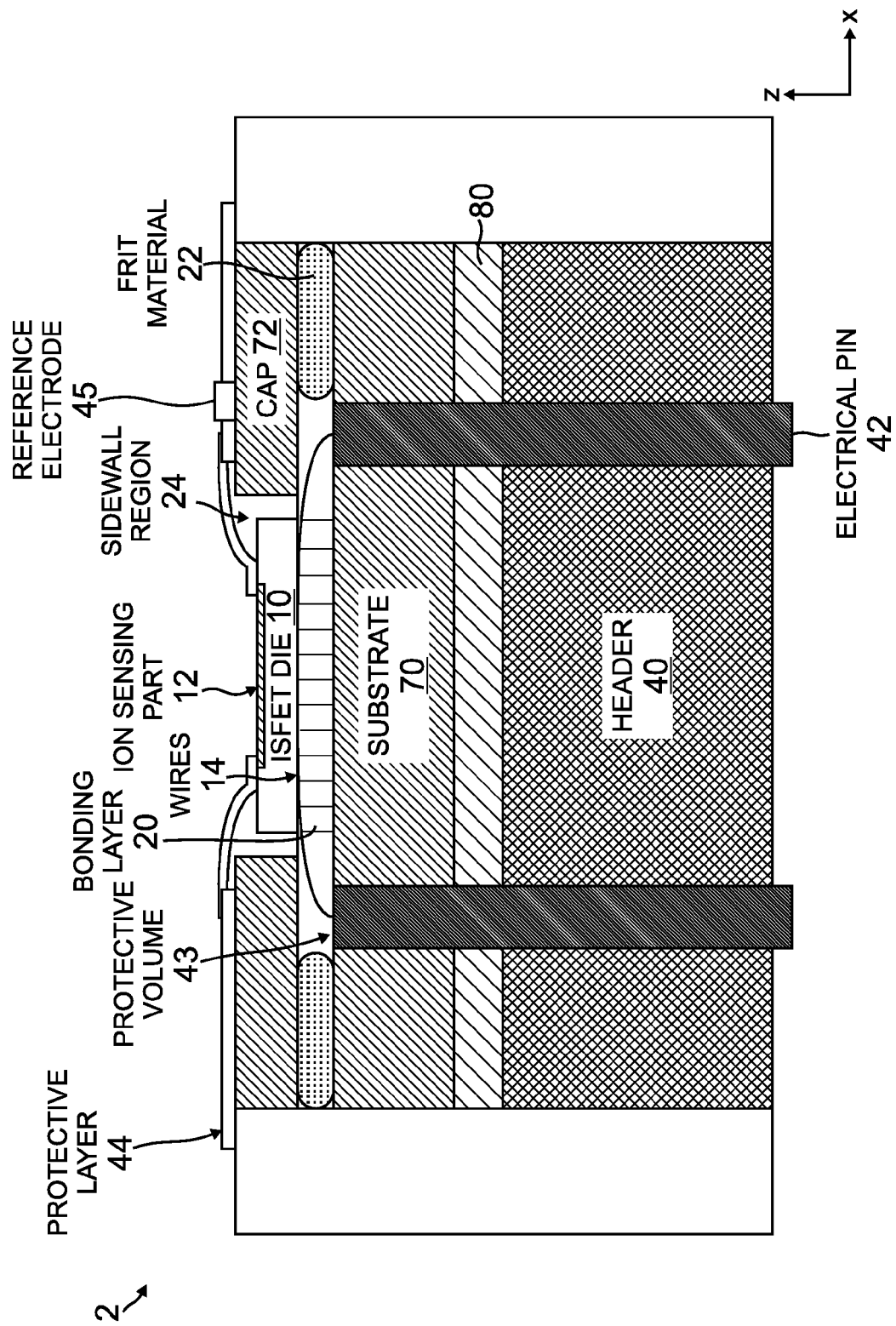
FIG. 1 is a cross-sectional view of an embodiment of a pH sensor comprising a bonding layer that attaches an ISFET die to a substrate.

FIG. 1 is a cross-sectional view of an example of a pH sensor 2. The pH sensor 2 includes an ISFET die 10 having an ion sensing part 12 fabricated therein for sensing a pH of a media in contact therewith. The pH sensor 2 is configured to expose at least a portion of the ion sensing part 12 to a media (e.g., sea or ocean water) in order to measure a pH thereof. The ISFET die 10 has a generally planar structure defining a first (major) surface, a second (major) surface which is reverse of the first surface, and one or more edges around the sides between the first surface and the second surface. The first surface of the ISFET die 10 has the ion sensing part 12 fabricated therein.

The ISFET die 10 is mounted to a substrate 70 which provides mechanical support to the ISFET die 10. The substrate 70 is a generally planar structure having a third (major) surface, a fourth (major) surface reverse of the third surface, and one or more edges around the sides between the third surface and the fourth surface. The second surface of the ISFET die 10 is bonded to the third surface of the substrate 70. In some examples, substrate 70 has substantially isotropic mechanical properties, wherein the coefficient of thermal expansion (CTE) of the substrate 70 in all directions parallel with a plane defined by the planar structure is substantially the same. In such examples, the substrate 70 may be a ceramic formed of aluminum oxide or aluminum nitride. In other examples, the substrate 70 has anisotropic (e.g., orthotropic) mechanical properties in directions parallel with the plane defined by the planar structure (See FIGS. 9A-9B). Substrate 70 can be mounted to a header 40. In some examples, substrate 70 is mounted to a header with a layer 80 disposed between substrate 70 and header 40. In an example, layer 80 may be formed of epoxy. In other examples, substrate 70 is mounted directly to header 40 without a layer of 80 disposed between substrate 70 and header 40.

Substrate 70 also defines through-holes for one or more electrical pins 42. One or more wires 14 provide an electrical connection between the ISFET die 10 and circuitry external to die 10. Wires 14 may also be bonded to at least one electrical pin 42. In one example, embedding wires 14 in a bonding agent material of a bonding layer 20 (discussed below) may provide increased protection of one or more wires 14 from temperature and pressure changes. Additionally, in a further example, wires 14 may be bonded to one or more electrical pins 42. A protective volume 43, which may comprise a partial vacuum, may be formed around the wire bond between wire 14 and at least one electrical pin 42.

In an example, pH sensor 2 also comprises cap 72 positioned around the ISFET die 10. In one example, cap 72 comprises the same composition as substrate 70. In other examples, cap 72 may comprise a different material than substrate 70. In some examples, substrate 70 and cap 72 provide rigid support for the ISFET die 10 to reduce the repeatable strains induced due to pressure and temperature changes. In some examples, a protective layer 44 may be formed on cap 72 and part of the ISFET die 10. In one example, protective layer 44 protects the pH sensor by shielding the bonding agent material of bonding layer 20 from long-term degradation due to exposure to salt water. In an example, protective layer 44 may be approximately chemically inert when immersed in salt water.

In the example shown in FIG. 1, pH sensor 2 comprises a frit material 22 disposed in one or more areas between substrate 70 and cap 72, bonding the substrate 70 to the cap 72. pH sensor 2 further comprises a bonding layer 20 disposed between the ISFET die 10 and the substrate 70. Bonding layer 20 bonds substrate 70 to the ISFET die 10. In some examples, bonding layer 20 may include one or more strips of one or more compositions of bonding agent material. In some examples, bonding layer 20 may include a homogenous composition of bonding agent material to bond the substrate 70 to the ISFET die. In other examples, bonding layer 20 may include a single composition of anisotropic material. In an example, substrate 70 may be bonded to the ISFET die 10 using the techniques of anodic bonding, eutectic bonding or adhesive bonding.

The accuracy of conventional pH sensors may be limited by measurement error induced by mechanical stresses associated with use in environments such as deep seas, and by packaging stresses associated with making the sensor strong enough to operate over a wide pressure variation. These errors may be caused by the anisotropic piezoresistance properties of the ISFET die 10. In particular, mechanical stresses on the ISFET die 10 can alter the electrical carrier transport through the ISFET die 10.

The subject matter described herein provides a pH sensor 2 that reduces piezoresistive pH sensor errors by reducing the pressure and temperature induced mechanical stresses on the ISFET die 10. In particular, the pH sensors described herein maintain the piezoresistance of the ISFET die from the drain to the source by inducing a force on the ISFET die 10 that is dependent on pressure and temperature, and counteracts at least a portion of other pressure and temperature induced mechanical forces on the ISFET die 10. This counteracting pressure and temperature dependent force is induced by a difference in a coefficient of thermal expansion (CTE), or a difference in the elastic modulus, or a difference in the Poisson ratio in at least one direction between the ISFET die 10 and either the bonding layer 20 or the substrate 70 or both; and is also referred to herein as the "CTE mismatch effect."

Turning to FIG. 11, shown in FIG. 11 is an example of a mathematical model of the CTE mismatch effect over a pressure and temperature range. In the example shown in FIG. 11, State 1 and State 2 denote the piezoresistance of the ISFET die at temperatures $T_1$ and $T_2$, respectively. As shown in FIG. 11, the CTE mismatch effect is used to reduce change in the piezoresistance from the drain to the source over a pressure and temperature range. Ideally, the piezoresistance change between any two pressures and temperatures in the pressure and temperature range is zero as shown in FIG. 11 (State 1≈State 2); however, in practice there will likely be some change in piezoresistance. At State 1, the ISFET die 10 has an initial piezoresistance coefficient matrix, $\pi_1$, at an initial temperature $T_1$. At State 1, an initial stress vector, $\sigma_1$, is the stress generated on the ISFET die at the pressure and temperature of state 1. Stress, $\sigma_1$, is dependent on the Elastic Modulus $E_1$, the Poisson Ratio $PR_1$, and strain $\epsilon_1$ of the ISFET die 10. Strain, $\epsilon_1$, is dependent on coefficient of thermal expansion $CTE_1$. In the example shown in FIG. 11, the piezoresistance coefficient $\pi$ of the ISFET die 10 changes with change in pressure and temperature.

As shown in FIG. 11, at $T_2$, the piezoresistance of the ISFET die is dependent on piezoresistance coefficient matrix $\pi_2$ and stress vector $\sigma_2$. Stress vector $\sigma_2$ is a net stress resulting from environmental stress $\sigma_{2a}$ and counteracting stress $\sigma_{2b}$. Environmental stress $\sigma_{2a}$ is generated on the ISFET die 10 due to pressure and temperature variations in the environment. The piezoresistance coefficient $\pi_2$ and the environmental stress $\sigma_{2a}$ would result in a piezoresistance of the ISFET die 10 in State 2 that is different from its piezoresistance in State 1. In order to maintain the piezoresistance of the ISFET die 10 from drain to source at two different temperatures, a counteracting stress $\sigma_{2b}$ can be generated on the ISFET die 10 that opposes at least a portion of the environmental stress $\sigma_{2a}$. The resulting net stress vector $\sigma_2$ is closer in value to the initial stress matrix, $\sigma_1$.

This counteracting stress $\sigma_{2b}$ may be generated by tailoring either the bonding layer 20 or the substrate 70 or both. In particular, the volume change of the bonding layer 20 or the substrate 70 or both as the temperature changes is used to induce the counteracting stress $\sigma_{2b}$ on the ISFET die 10 that maintains the piezoresistance from the drain to the source. The counteracting stress $\sigma_{2b}$ may be caused by the effective magnitude and directional dependence of the elastic modulus ($E_2$), the effective magnitude and directional dependence of the Poisson ratio ($PR_2$), or the effective magnitude and directional dependence of the coefficient of thermal expansion ($CTE_2$) on the ISFET die 10. In some examples, the piezoresistive sensitivity of the ISFET die 10 after the CTE mismatch effect may be reduced to tenth of its initial piezoresistive sensitivity. For example, in an ISFET die with 1-2% piezoresistance, the relative percent change in resistance due to piezoresistance, $\Delta R/R$, from the drain to the source may be maintained within 0.1-0.2% over the pressure and temperature range. In an example, the change in piezoresistance from the drain to the source may be less than 0.5%.

Figure 9A:
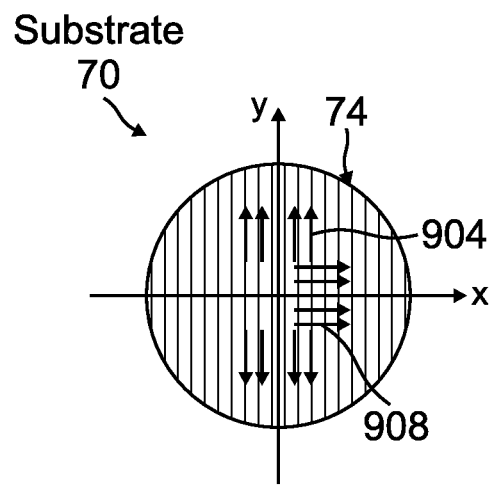
FIG. 9A illustrates an embodiment of forming the substrate layer from an anisotropic single crystal form of solid.
Figure 9B:
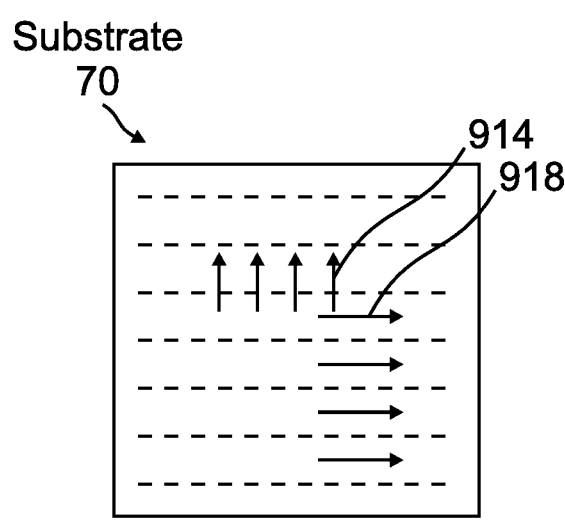
FIG. 9B illustrates an embodiment of forming the substrate layer using an aligned fiber composite.
Figure 10:
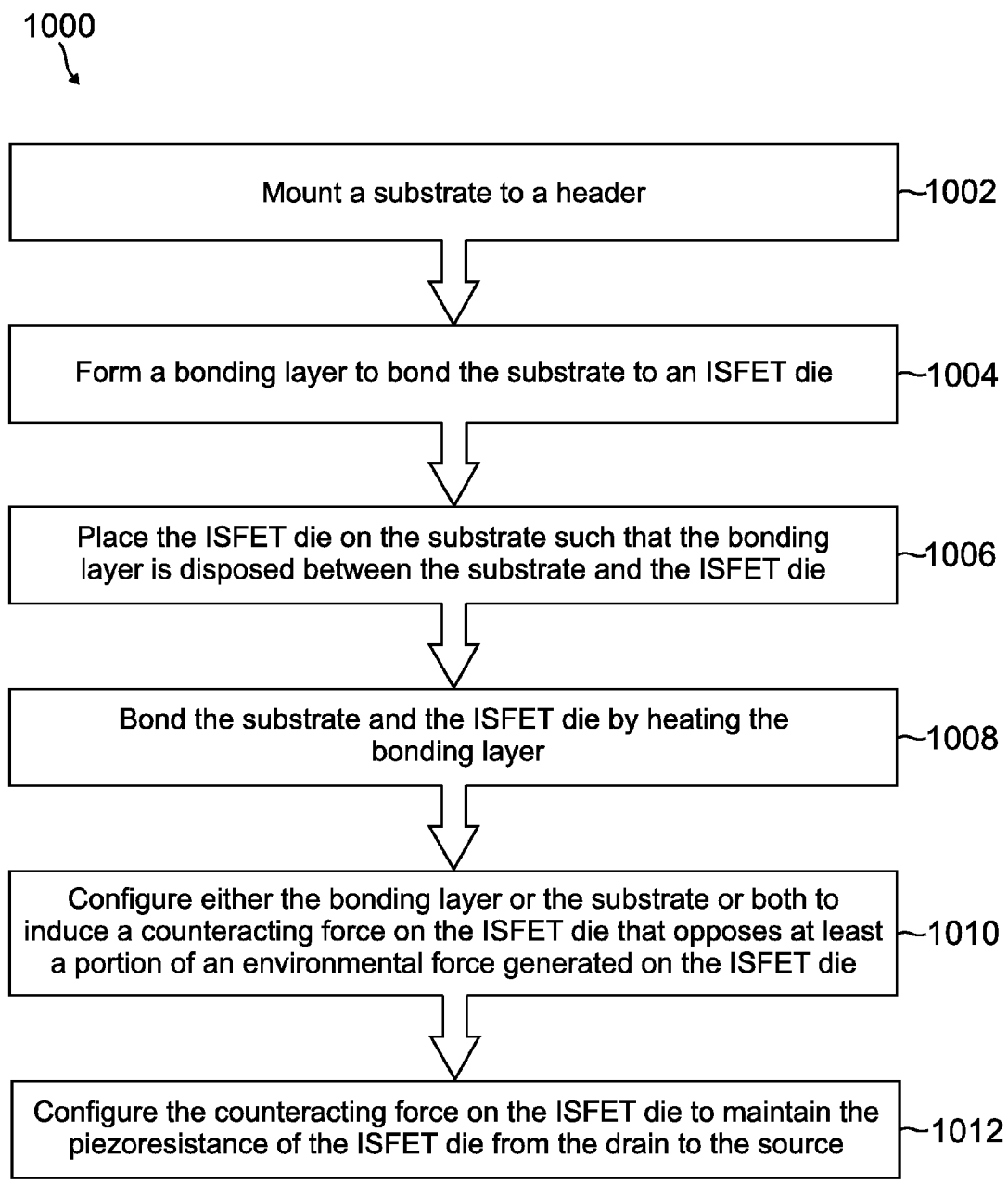
FIG. 10 is a flow diagram of another embodiment of a method to form a pH sensor of FIG. 1.

One way of achieving a CTE mismatch effect is by selecting a composition of anisotropic material that responds to pressure and temperature changes by inducing forces of different magnitudes in different directions (See FIGS. 9-10). Such an effect is achieved by change in volume due to thermal expansion/contraction of either substrate 70 or bonding layer 20 or both with respect to the ISFET die 10. In some examples, anisotropic material is used to construct the substrate 70. Substrate 70 is oriented such that at different pressures and temperatures the force induced by substrate 70 during thermal expansion/contraction occurs in a direction which will counteract other mechanical forces on the ISFET die 10. In some implementations of the embodiments described with respect to FIGS. 9-10, the bonding layer 20 comprises a composition of homogenous bonding agent material. In an example, substrate 70 is orthotropic. In other examples, bonding layer 20 is composed of anisotropic bonding agent material so that it responds to pressure and temperature changes by inducing a force of different magnitudes in different directions to counteract other mechanical forces on the ISFET die 10. In a further example, the bonding agent material has orthotropic mechanical properties.

In a further embodiment of the anisotropic configuration, the CTE mismatch effect is achieved when the substrate 70 or the bonding layer 20 has a CTE in one direction that is different from its CTE in a second direction such that at different pressures and temperatures the force induced by substrate 70 or the bonding layer 20 counteracts other mechanical forces on the ISFET die 10. The volume of the substrate 70 or the bonding layer 20 changes depending on its CTE. In some examples, the elastic modulus of the substrate 70 or the bonding layer 20 is constant in all directions at varying pressures and temperatures. In some examples, the Poisson ratio of the substrate 70 or the bonding layer 20 is constant in all directions at varying pressures and temperatures.

In yet another embodiment of the anisotropic configuration, the CTE mismatch effect is achieved when the substrate 70 or the bonding layer 20 has an elastic modulus in one direction that is different from its elastic modulus in a second direction such that at different pressures and temperatures the force induced by the substrate 70 or the bonding layer 20 counteracts other mechanical forces on the ISFET die 10. The volume of the substrate 70 or the bonding layer 20 changes depending on its elastic modulus. In some examples, the CTE of the substrate 70 or the bonding layer 20 is constant in all directions at varying pressures and temperatures. In some examples, the Poisson ratio of the substrate 70 or the bonding layer 20 is constant in all directions at varying pressures and temperatures.

In still another embodiment of the anisotropic configuration, the CTE mismatch effect is achieved when the substrate 70 or the bonding layer 20 has Poisson ratio in one direction that is different from its Poisson ratio in a second direction such that at different pressures and temperatures the force induced by substrate 70 or the bonding layer 20 counteracts other mechanical forces on the ISFET die 10. The volume of the substrate 70 or the bonding layer 20 changes depending on its Poisson ratio. In some examples, the elastic modulus of the substrate 70 or the bonding layer 20 is constant in all directions at varying pressures and temperatures. In some examples, the CTE of the substrate 70 or the bonding layer 20 is constant in all directions at varying pressures and temperatures.

Another way of achieving a CTE mismatch effect is by selecting a material for the bonding layer 20 based on its CTE and disposing one or more strips of the material between the substrate 70 and the ISFET die 10 in a pattern (See FIGS. 2-8). The orientation of the one or more strips can be selected such that the force induced by the material during thermal changes occurs in a direction which will counteract other mechanical forces on the ISFET die 10. In some implementations of the embodiments described with respect to FIGS. 2-8, substrate 70 has isotropic mechanical properties. Substrate 70 may be composed of a ceramic such as aluminum oxide or aluminum nitride.

In an example, the orientation of the one or more strips is selected to achieve biaxial loading of the ISFET die 10. In particular, the CTE mismatch effect can induce an orthogonal strain generated due to the CTE mismatch of material(s) of the bonding layer 20 and the ISFET die. A beneficial biaxial force can be induced by using two different compositions of glass fits or bonding agents disposed between the sensor die and its mounting substrate. These compositions may be selected based on their coefficient of thermal expansion (CTE) so that at different temperatures the two materials induce different thermal strains into the die to produce biaxial loading conditions.

Figure 2:
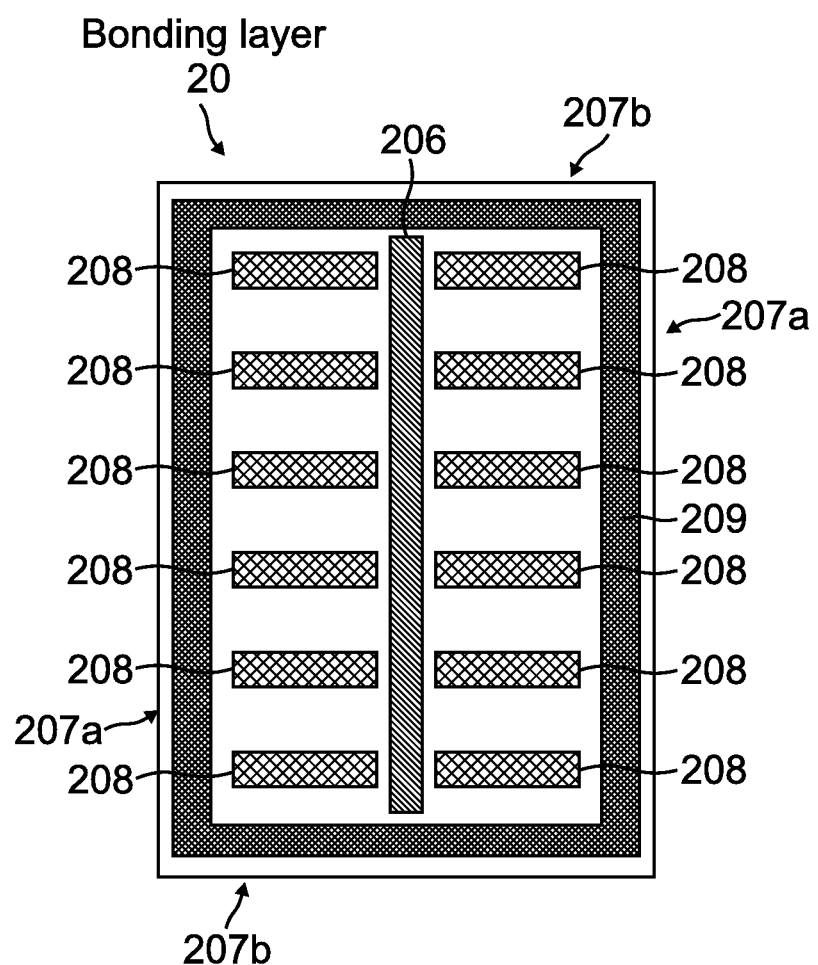
FIG. 2 is a top view of an embodiment of the bonding layer of FIG. 1.

FIG. 2 is a top view of an embodiment illustrating an exemplary layout of bonding layer 20 that is disposed on the second surface of the ISFET die 10 (shown in FIG. 1). Bonding layer 20 comprises one or more strips of bonding agent material disposed in a pattern between the second surface of the ISFET die 10 and the third surface of the substrate 70. In this example, the second surface (and, therefore, the ISFET 10 as a whole) has a generally rectangular shape, with a first strip 206 of a first composition of bonding agent material disposed in a direction parallel to a long edge 207a of the ISFET die 10. As shown in FIG. 2, multiple second strips 208 of a second composition of bonding agent material are disposed orthogonally to strip 206 and parallel to a short edge 207b of the ISFET die 10. In this example, first strip 206 is longer than second strips 208, which are comparatively shorter and disposed on either side of first strip 206. One or both of the first and second bonding agent material may be composed of a glass frit. Other bonding agent materials may also be used for either the first strip or the second strip. The second composition of bonding agent material used for the second strips 208 has a coefficient of thermal expansion (CTE) that is different from a CTE of the first composition of bonding agent material used for the first strip 206. Accordingly, at different temperatures the two bonding agent materials will induce different thermomechanical force onto the ISFET die 10. Since the first strip 206 is oriented in a different direction (e.g., orthogonally) than the second strips 208, the combined forces induced by the strips 206, 208 will be greater in one of the directions, which will achieve the CTE mismatch effect.

As shown in FIG. 2, an embodiment may further include a perimeter section 209 of a bonding agent material disposed along a perimeter 207 of the ISFET die 10. In this example, perimeter section 209 is disposed to provide edge support and sealing. However, in another example, strips of two different bonding agent materials with different CTE may be disposed along the perimeter so that the thermomechanical force induced onto the ISFET die is greater in one of the directions, and achieves the CTE mismatch effect (See FIG. 5D). Further, in the example shown in FIG. 2, the bonding agent material disposed in perimeter section 209 has a CTE that is different from the bonding agent materials used for the first strip 206 or second strips 208. However, as shown in the following examples in FIGS. 3A-3D, the bonding agent material of the perimeter section may be of the same composition as one of the bonding agent materials of the first strip 206 or second strips 208.

Figure 3A:
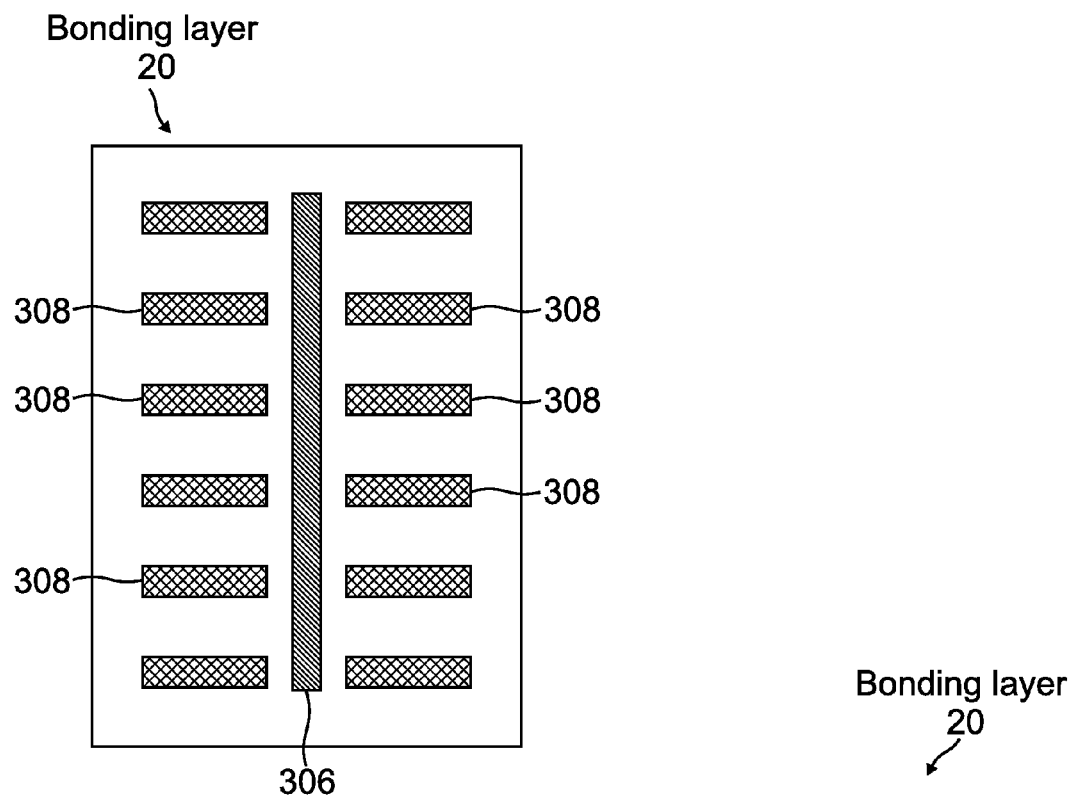
FIGS. 3A-3D are top views of other embodiments of the bonding layer of FIG. 1.
Figure 3B:
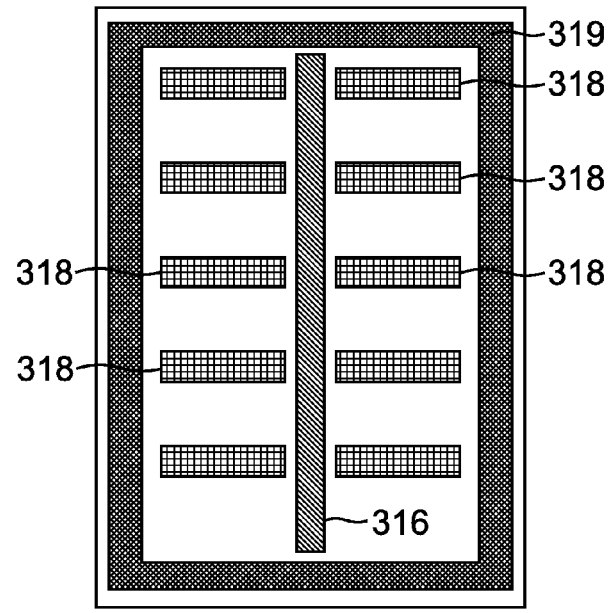
Figure 3C:
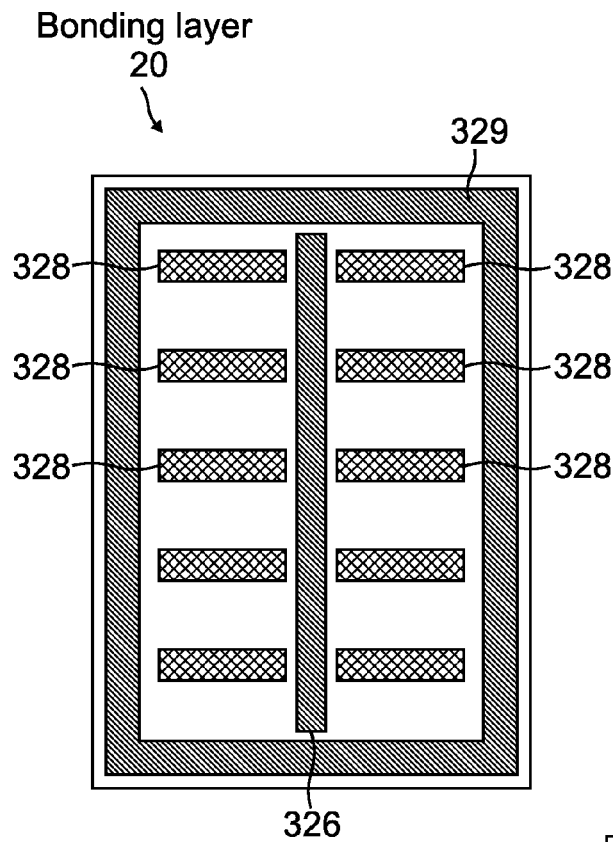
Figure 3D:
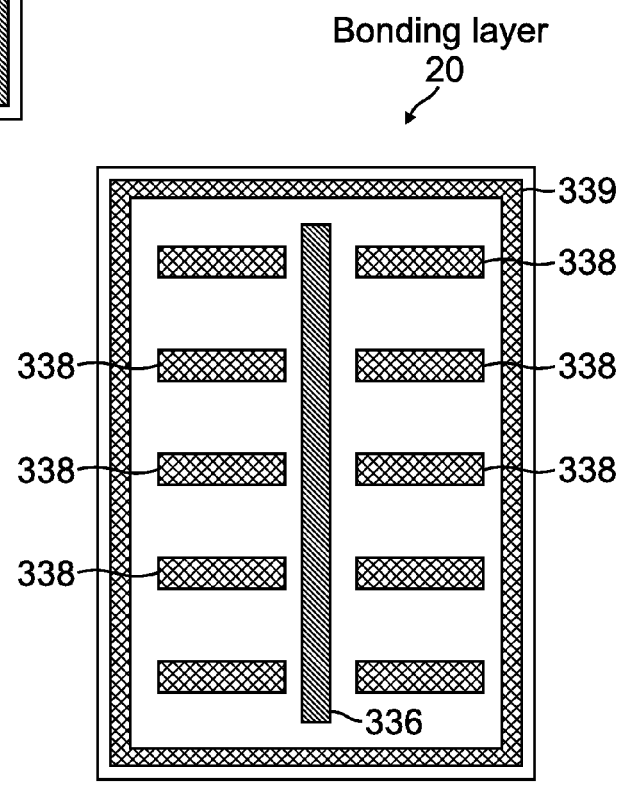

FIGS. 3A-3D illustrate various examples of bonding layer 20 using different compositions of bonding agent materials along the perimeter of the ISFET die 10. FIG. 3A illustrates an example of bonding layer 20 comprising of a pattern without a perimeter section. In FIG. 3B, the composition of bonding agent material used for the first strip 316 has a CTE different from the composition of bonding agent material used for the second strips 319. The composition of bonding agent material used in perimeter section 319 does not have the same CTE as the composition of bonding agent material used for the strip 316 or the strips 318. In FIG. 3C, the composition of bonding agent material used for a perimeter section 329 along the perimeter of the ISFET die 10 has the same CTE as the one used for the first strip 326, but not the same CTE as the one used for the second strips 328. In FIG. 3D, the composition of bonding agent material used for a perimeter section 339 has the same CTE as the composition of bonding agent material used for the second strips 338, but not the same CTE as the one used for the first strip 336. In another example, if a third composition of bonding agent material is used for additional strips to achieve the CTE mismatch effect, it is to be understood that a perimeter section may be disposed using that third composition of bonding agent material.

Figure 4A:
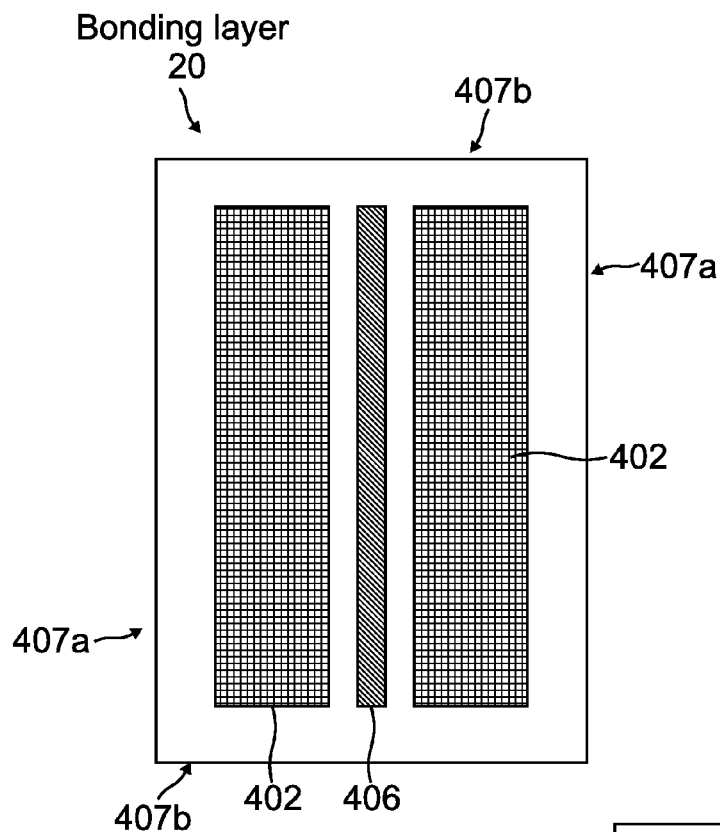
FIGS. 4A and 4B are top views of yet other embodiments of the bonding layer of FIG. 1, where the bonding layer attaches the substrate to the ISFET die using a single bonding agent material.
Figure 4B:
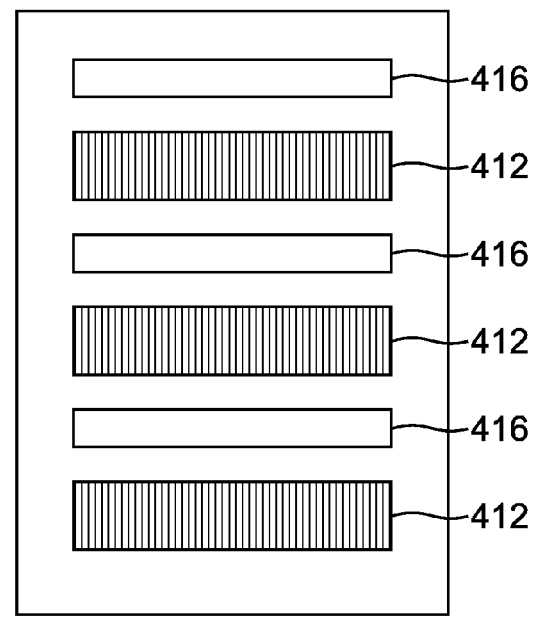

FIGS. 4A-4B are embodiments of bonding layer 20 disposed between the substrate 70 and the ISFET die 10 (shown in FIG. 1), where the bonding layer 20 comprises one or more strips of only one composition of bonding agent material. In an example shown in FIG. 4A, a strip 406 of a composition of bonding agent material is disposed parallel to an edge 407a of the ISFET die 10 (shown in FIG. 1). A second bonding agent is not used. In order to support ISFET die 10, inert material 402 is deposited in the remaining portions of bonding layer 20. Inert material 402 does not exert any CTE force on to the ISFET die 10 but may generate limited shear stress on the die through friction. As shown in FIG. 4B an embodiment may include multiple strips 416 of a composition of bonding agent material disposed perpendicular to an edge 417a of the ISFET die 10, and inert material 412 deposited in the remaining portions of bonding layer 20. In this example, ISFET die 10 is supported by inert material 412, but may generate limited shear stress on to the ISFET die 10 through friction. In the embodiments shown in FIGS. 4A and 4B, the CTE mismatch effect is achieved by orienting the strip(s) of the composition of bonding agent material so that the force induced by the bonding agent material counteracts with other mechanical forces on the ISFET die 10. It is to be understood that in other examples the bonding agent material and the inert material may be configured in patterns other than the ones shown in FIGS. 4A and 4B to achieve the CTE mismatch effect.

FIGS. 5A-5E are different embodiments of bonding layer 20 illustrating various patterns formed using compositions of bonding agent materials with different CTE such that at different temperatures the bonding agent materials will induce different thermomechanical force into the ISFET die 10 to achieve the CTE mismatch effect. For example, in FIG. 5A, first strip 506 is disposed using a composition of bonding agent material that may include, but is not limited to, a glass frit. Multiple second strips 508 are disposed in a direction orthogonal to first strip 506. The CTE of the composition of bonding agent material used to dispose the multiple second strips 508 is different from the CTE of the composition of bonding agent material used to dispose first strip 506. At different temperatures, the combined force induced by strips 508 and 506 will be greater in one direction and will achieve the CTE mismatch effect.

Figure 5A:
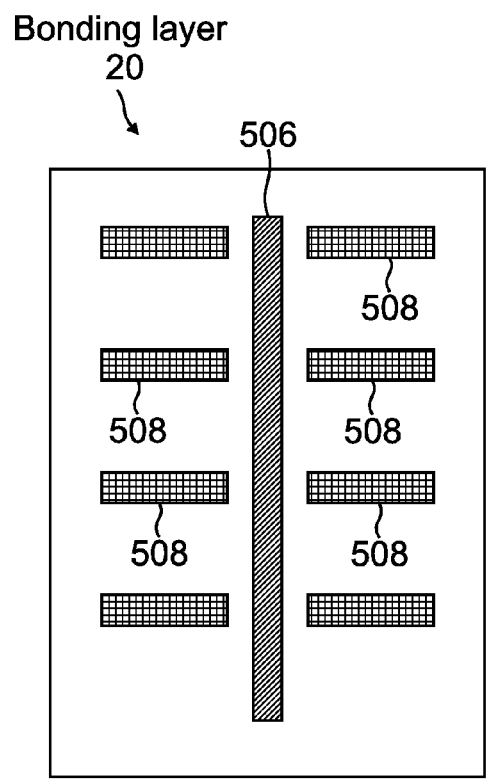
FIGS. 5A-5E are top view of still other embodiments of the bonding layer of FIG. 1.
Figure 5B:
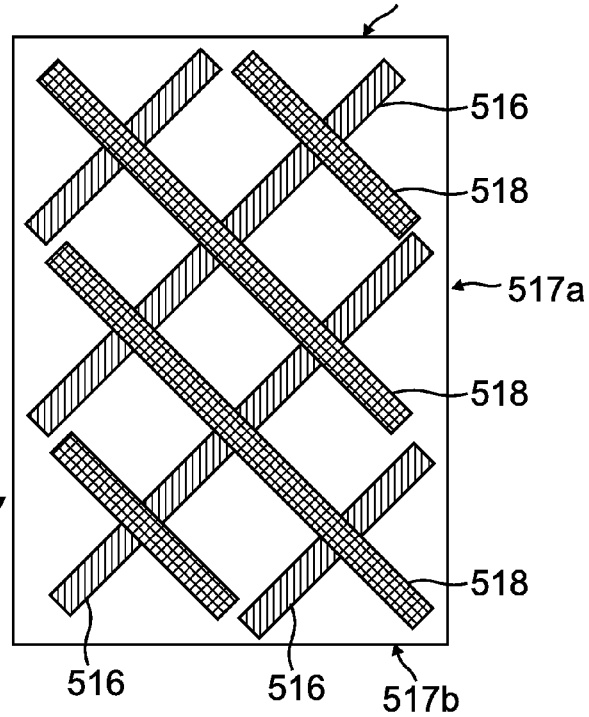
Figure 5C:
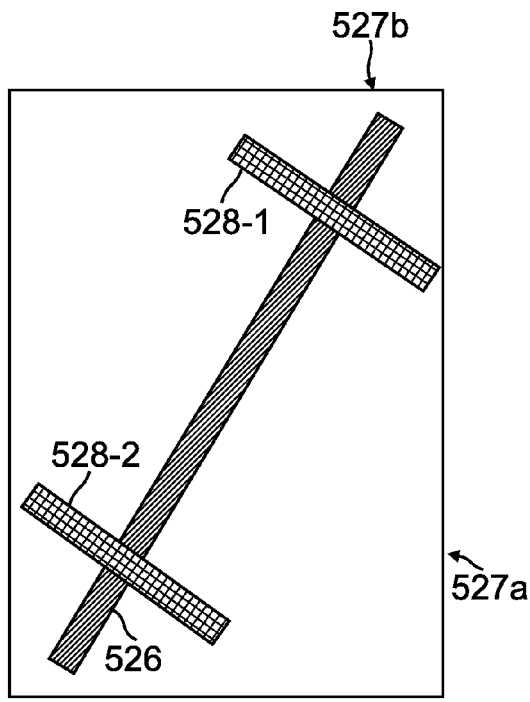

In FIG. 5B, multiple first strips 516 are disposed in a direction diagonal to edges 517a and 517b of the ISFET die 10. Multiple second strips 518 are disposed in a direction orthogonal to multiple first strips 516 (also diagonal to edges 517a and 517b but in the opposite direction). Second composition of bonding agent material used to dispose multiple second strips 518 has a different CTE from a first composition of bonding agent material used to form multiple first strips 516, which induce different thermomechanical forces into the ISFET 10 at different temperatures in order to achieve the CTE mismatch effect. In another example shown in FIG. 5C, a single strip 526 is disposed in a direction diagonal to edges 527a and 527b of the ISFET die 10. Two strips 528-1 and 528-2 of a second composition of bonding agent material with a CTE different from the first composition of bonding agent material used to dispose single strip 526 are disposed orthogonally to strip 526.

Figure 5D:
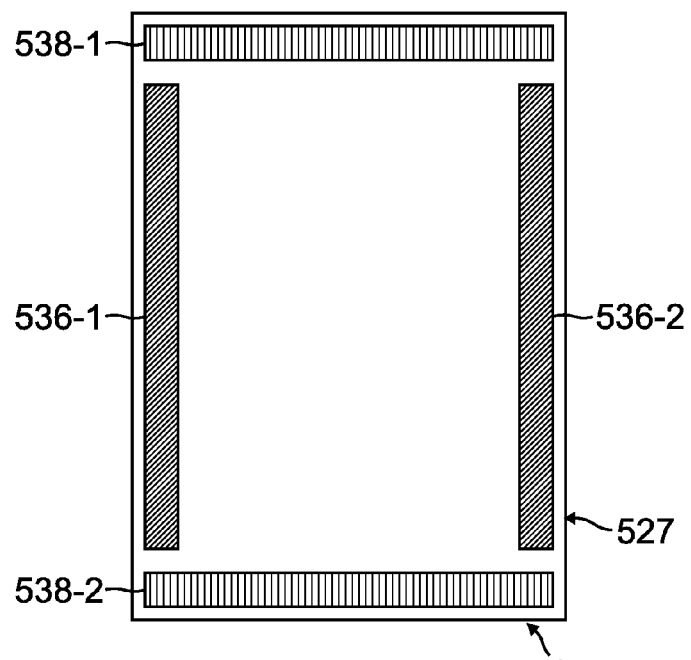

Another embodiment of bonding layer 20 is shown in FIG. 5D. In this example, the CTE mismatch effect may be achieved by disposing strips of two different bonding agent materials along the perimeter. As shown in FIG. 5D, strips 536-1 and 536-2 are disposed using a first composition of bonding agent material. Strips 538-1 and 538-2 are disposed using a second composition of bonding agent material. The first composition of bonding agent material used to dispose strips 538-1 and 538-2 is different from the second composition of bonding agent material used to dispose strip 536-1 and 536-2. Strips 536-1 and 536-2 are orthogonal to strips 538-1 and 538-2. At different temperatures, strips 536-1 and 536-2 will induce different thermomechanical force into the die than strips 538-1 and 538-2 producing biaxial loading conditions to achieve the CTE mismatch effect.

Figure 5E:
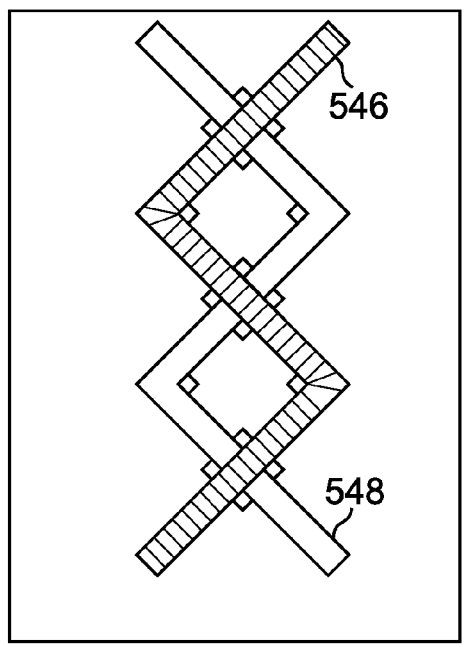

FIG. 5E illustrates an embodiment of bonding layer 20. In this example, first strip 546 is disposed in a zigzag. Second strip 548 is disposed in a zigzag in the opposite direction. In an example, corners of first strip 546 create a right angle. In an example, corners of second strip 548 also create a right angle. In a further example, first strip 546 and second strip 548 may be orthogonal to each other. A first composition of bonding agent material used to dispose first strip 546 has a different CTE from a second composition of bonding agent material used to dispose second strip 548 so that biaxial loading conditions are produced to achieve the CTE mismatch effect.

Figure 6:
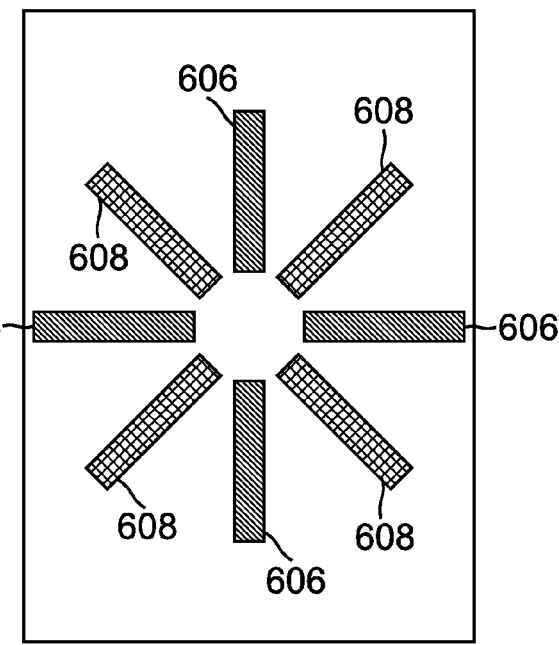
FIG. 6 is a top view of another embodiment of the bonding layer of FIG. 1, where the bonding layer includes strips of material that are non-orthogonal to one-another.
Figure 7A:
FIGS. 7A-7F illustrate different embodiments of a strip of bonding agent material disposed in the bonding layer of FIG. 1.
Figure 7B:
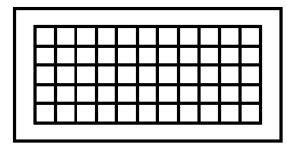
Figure 7C:
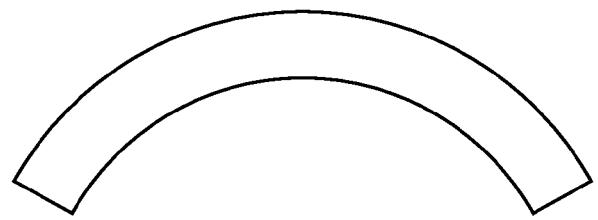
Figure 7D:
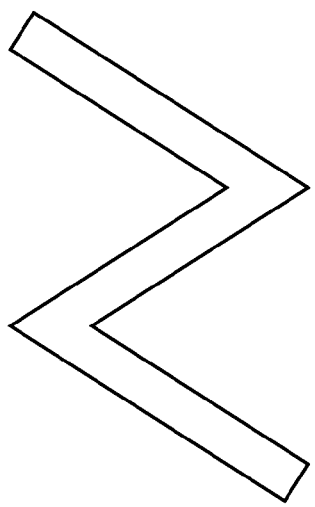
Figure 7E:
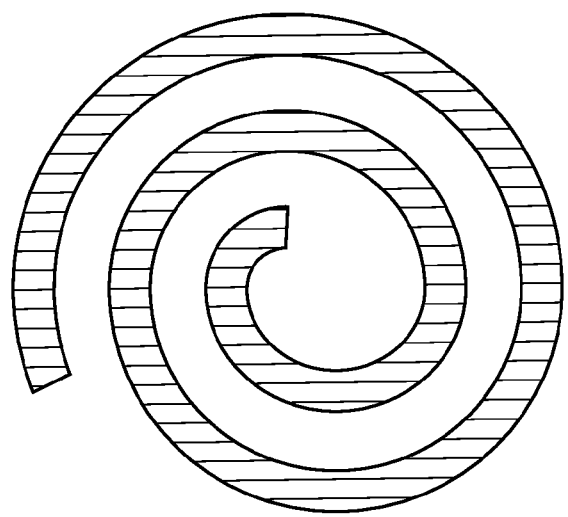
Figure 7F:
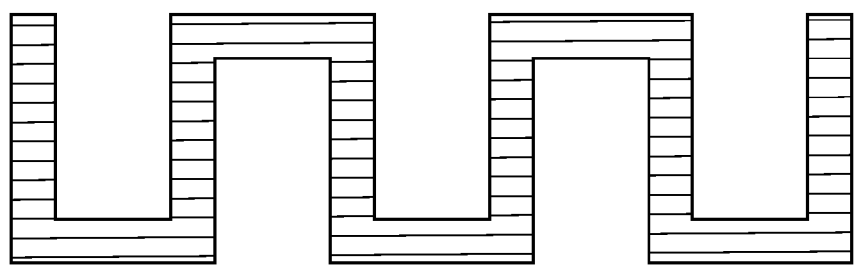

In some examples, the CTE mismatch effect may be achieved even when the strips are disposed in a radial or an axial pattern as opposed to being disposed orthogonally to each other (See FIG. 6). FIG. 6 illustrates an embodiment where strips of different compositions of bonding agent material may not be orthogonal to each other. Multiple first strips 606 are disposed of a first bonding agent material with a CTE different from a second bonding agent material used to dispose multiple second strips 608. First strips 606 and second strips 608 both induce two different thermomechanical forces into the ISFET die 10 to produce biaxial loading conditions in order to achieve the CTE mismatch effect. There may be additional strips of a third bonding agent material disposed in a radial pattern, which may induce a third force onto the die and produce the CTE mismatch effect because of the difference in CTE of the different compositions of bonding agent materials.

FIGS. 7A-7F illustrate different embodiments of a strip of bonding agent material disposed in bonding layer 20. In the present disclosure, a strip of bonding agent material refers to bonding agent material having a narrow and elongated shape. In some examples, a strip may be a linear strip, such as a long linear rectangular (shown in FIG. 7A) or a short rectangle (shown in FIG. 7B). In some examples, a strip may be non-linear. For example, a strip may be an arc of uniform width (shown in FIG. 7C), a spiral (shown in FIG. 7D), or a zigzag (shown in FIG. 7E). In some examples, a strip may be in waveform (square wave shown in FIG. 7F). It is to be understood that the definition of a strip is not limited by the examples shown in FIGS. 7A-7F.

Figure 8:
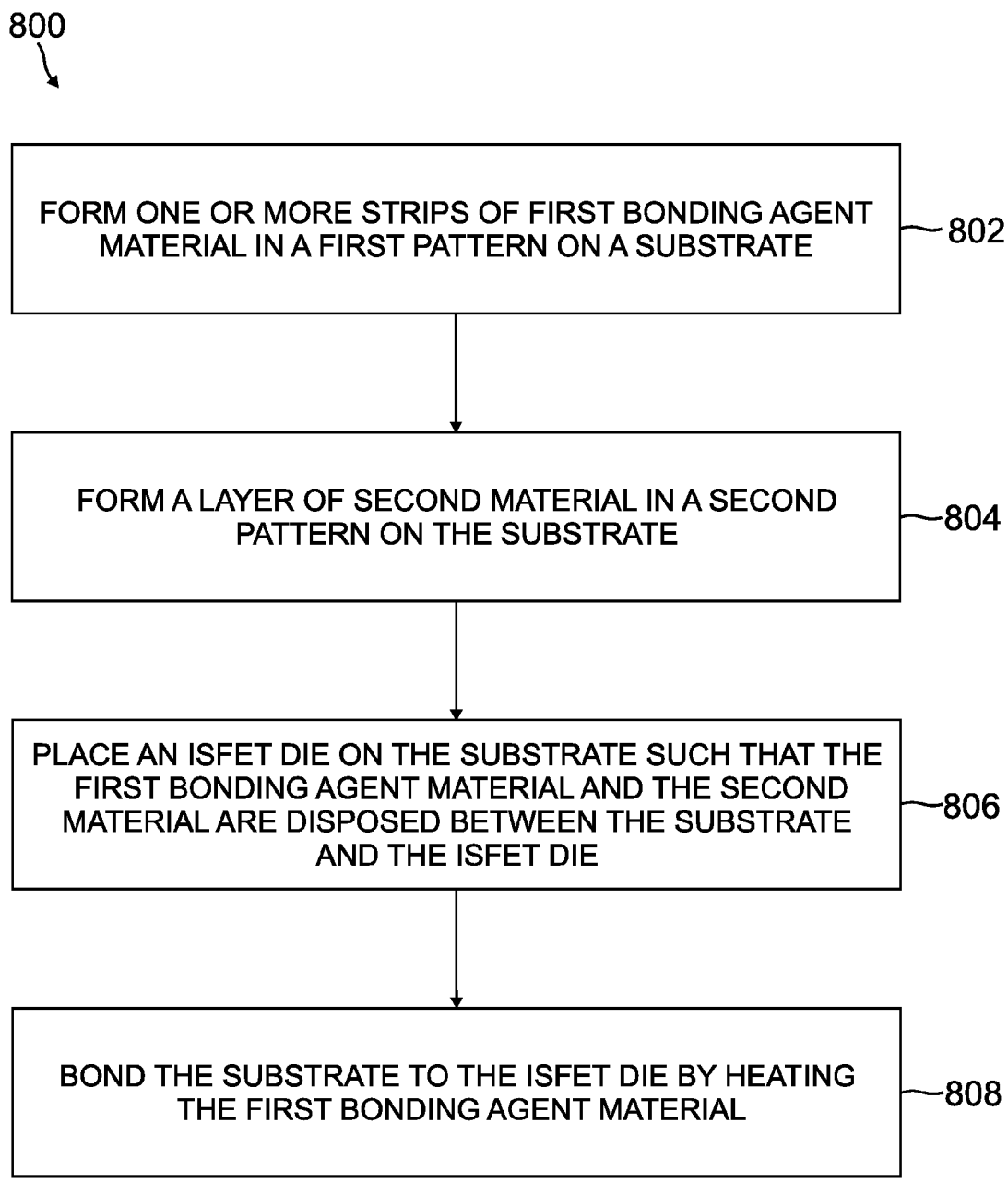
FIG. 8 is a flow diagram of one embodiment of a method to form the pH sensor of FIG. 1.

FIG. 8 is a flow diagram of one embodiment of a method 800 to manufacture a pH sensor. As discussed herein, method 800 is described with respect to the examples of the pH sensor shown in FIGS. 1-7. However, method 800 may apply to other sensor examples of the pH sensor as well. In the example shown in FIG. 8, method 800 comprises forming one or more strips of first bonding agent material in a first pattern on a substrate (802). The pattern formed in block 802 may be one described in the bonding layer embodiments of FIGS. 2-6. Block 802 may include forming one or more strips of first bonding agent material in a pattern that is not described in the above embodiments but achieves the CTE mismatch effect. The first bonding agent material in block 802 may be a glass frit.

Method 800 further comprises forming a second material in a second pattern on the substrate (804). Forming a second material in block 804 may include depositing an inert material, or forming one or more strips of a second bonding agent material that has a different CTE from the first bonding agent material used to form one or more strips in block 802. In some examples, the second bonding agent material in block 804 may be a glass frit. In a further example, block 804 may include forming one or more strips of the second bonding agent material orthogonally to one or more strips of first bonding agent material of block 802.

Method 800 further comprises placing the ISFET die on the substrate such that the first bonding agent material and the second material are disposed between the substrate and the ISFET die (806). Method 800 also comprises bonding the substrate to the ISFET die by heating the bonding agent material (808). The bonding agent material in block 808 may include a glass frit. In an example, heating the bonding agent material in block 808 may include melting the glass frit using a laser based glass frit curing technique.

In some examples, the first and second compositions of bonding agent material may be two different chemical compositions of epoxy. In other examples, the two different compositions of bonding agent material may start with same chemical composition of epoxy, but a filler material is added in the epoxy to form the second composition of bonding agent material such that the thermomechanical properties of the epoxy in the second composition are changed so that the second composition is heterogeneous, and the CTE mismatch effect is achieved. The filler material used to change the composition of epoxy may be beads, sphere, fibers, or other small particles. In some examples, the filler material may be made of glass. In other examples, a different material may be used for the filler material.

In a different configuration, the CTE mismatch effect may be achieved by using a substrate or a bonding layer with anisotropic mechanical properties. The substrate or the bonding layer has a different CTE, or a different elastic modulus or a different Poisson ratio in different directions and responds to temperature changes by inducing force of different magnitudes in different directions. In some examples, the substrate may be orthotropic. In some examples of this configuration, the bonding agent material disposed between the substrate and the ISFET die may be homogenous. In some examples, the bonding layer may have orthotropic mechanical properties. The differential force is transferred into the ISFET die through the homogenous bonding agent producing biaxial loading conditions to achieve the CTE mismatch effect.

In some examples, substrate 70 (shown in FIG. 1) may be constructed by growing a sheet of single crystal of solid material such that the solid material has anisotropic mechanical properties in the single crystal form. In some examples, the substrate 70 may be orthotropic. In some examples, the substrate 70 may be constructed from single crystal silicon, single crystal aluminum or single crystal copper. In other examples, single crystal forms of other materials may be used to construct the substrate. FIG. 9A is a top view of substrate 70 illustrating the directions and magnitudes in which the forces are generated. As illustrated in FIG. 9A, substrate 70 is fabricated by growing a sheet of anisotropic single crystal of solid material. At different temperatures the substrate generates force of two different magnitudes. In this example, a force 904 is generated in the direction of the y-axis and another force 908 is generated in the direction of the x-axis, which is orthogonal to the y-axis. Force 904 is of a different magnitude than force 908 because the CTE of the anisotropic single crystal of the solid material shown in FIG. 9A is different in the x-direction as opposed to the y-direction. The resulting differential force will achieve the CTE mismatch effect.

In other examples, substrate 70 or bonding layer 20 may be constructed of an aligned fiber composite. The fibers are intentionally aligned to create a composition with anisotropic mechanical properties. In some examples, the substrate 70 may be orthotropic. In some examples, bonding layer 20 may be formed to have orthotropic mechanical properties. For example, the substrate 70 or the bonding layer 20 may be formed of a carbon fiber and epoxy composite where the carbon fibers are aligned in epoxy. In some examples, the aligned fiber composite may be formed of carbon fibers, boron fibers, glass fibers or graphite fibers that are aligned in epoxy, resin, thermoplastic matrix or thermoset matrix. In other examples, the aligned fiber composite may be a metal matrix composite that may include aluminum oxide fibers or silicon carbide fibers aligned in aluminum metal. FIG. 9B illustrates an example of the alignment of fibers to create an orthotropic composite. In the illustrated example, the preferential direction of the composite is the direction in which the fibers are aligned. A force 918 is generated in the preferential direction. In order to achieve the CTE mismatch effect, a force 914 orthogonal to its preferred direction is generated to produce biaxial loading conditions.

FIG. 10 is a flow diagram of one embodiment of a method 1000 to manufacture a pH sensor in accordance with the present description. As discussed herein, method 1000 is described with respect to the examples of the pH sensor shown in FIGS. 1 and 9A-9B. However, method 1000 may apply to other sensor examples of the invention as well. In an example, as shown in FIG. 10, method 1000 comprises mounting a substrate on to a header (1002). Additionally, in some examples, mounting the substrate on to the header in block 1002 may include constructing a substrate by growing a sheet of single crystal of a solid material such that the solid material has anisotropic mechanical properties in its single crystal form. This solid material may include single crystal silicon, single crystal aluminum or single crystal copper. In other examples, mounting the substrate over the header may include constructing a substrate of aligned fiber composite with anisotropic mechanical properties.

Method 1000 further comprises forming a bonding layer on to the substrate to bond the substrate to an ISFET die (1004). In an example, the bonding layer may include a composition of bonding agent material that is a glass frit. Method 1000 further comprises placing the ISFET die on the substrate such that the bonding layer is disposed between the substrate and the ISFET die (1006). Method 1000 further comprises bonding the substrate to the ISFET die by heating the bonding layer (1008).

Method 1000 further comprises configuring either the bonding layer or the substrate or both to induce a counteracting force on the ISFET die that opposes at least a portion of the environmental force generated on the ISFET die due to the pressure and temperature change across the pressure and temperature range (1010). Finally, method 1000 comprises configuring the counteracting force on the ISFET die to maintain the change in piezoresistance of the ISFET die from the drain to the source to less than 0.5% over the pressure and temperature range (1012).

EXAMPLE EMBODIMENTS

Example 1 includes a pH sensor comprising: a substrate; an ion sensitive field effect transistor (ISFET) die including an ion sensing part that responds to pH, wherein the ISFET die is bonded to the substrate; wherein the ion sensing part of the ISFET die is configured to be exposed to a medium, and wherein the ion sensing part outputs a signal related to a pH level of the medium; and one or more strips of at least one composition of a bonding agent material disposed in a first pattern between the substrate and the ISFET die.

Example 2 includes the pH sensor of Example 1, further comprising: one or more strips of a second composition of a bonding agent material disposed between the substrate and the ISFET die in a second pattern, wherein the coefficient of thermal expansion (CTE) of the second composition is different from the CTE of the at least one composition such that at different temperatures the two materials induce forces on the die in different directions.

Example 3 includes the pH sensor of Example 2, wherein the second pattern further comprises one or more strips of the second composition of bonding agent material that are disposed orthogonally to the one or more strips disposed in the first pattern of the at least one composition.

Example 4 includes the pH sensor of any of Examples 1-3, further comprising: an inert material, wherein the inert material supports a portion of the ISFET die and does not exert a force due to CTE on the said portion of the ISFET die.

Example 5 includes the pH sensor of any of Examples 1-4, wherein, the at least one composition of a bonding agent material comprises a glass frit.

Example 6 includes the pH sensor of Example 1, wherein the ISFET die is bonded to the substrate by anodic bonding, eutectic bonding, or adhesive bonding.

Example 7 includes the pH sensor of any of Examples 1-6, further comprising: a third composition of a bonding agent material, wherein the third composition of bonding agent material is disposed along the perimeter of the said ISFET die.

Example 8 includes the pH sensor of Example 7, wherein the third composition of a bonding agent material is the same as the at least one composition of a bonding agent material.

Example 9 includes the pH sensor of any of Examples 1-8, wherein the substrate comprises a base substrate and a cap formed over the base substrate, the pH sensor further comprising: a protective layer formed over at least a portion of an outer surface of the ISFET die and at least a portion of the cap substrate; a cover member mechanically coupled to the protective layer, wherein the cover member houses the ISFET die and the substrate, and wherein the cover member defines an opening proximate to the ion sensing part; a header, wherein the substrate is mounted to the header; a reference electrode that provides a reference voltage; and at least one electric pin coupled to the ISFET die via a wire.

Example 10 includes the pH sensor of any of Examples 1-4, wherein the at least one composition of a bonding agent material comprises an epoxy with filler material.

Example 11 includes a method of manufacturing a pH sensor, the method comprising: forming one or more strips of a first bonding agent material on a substrate; forming a layer of second material on the substrate in a second pattern; placing the ISFET die on the substrate such that one or more strips of the first pattern and the layer of second material are disposed between the substrate and the ISFET die; and bonding the substrate to the ISFET die by heating the first bonding agent.

Example 12 includes a method of Example 11, wherein forming a layer of the second material on the substrate further comprises forming one or more strips of a second bonding agent material on a substrate in a second pattern, wherein the coefficient of thermal expansion (CTE) of the second bonding agent is different from the CTE of the first bonding agent material.

Example 13 includes a method of Example 11 or Example 12, wherein the first bonding agent material comprises a glass frit.

Example 14 includes a method of any of Examples 11-13, wherein heating the first bonding agent further comprises melting the different compositions of frit materials using a laser based glass frit curing technique.

Example 15 includes a method of Example 12, further comprising: forming one or more strips of second pattern orthogonally to one or more strips of the first pattern.

Example 16 includes a method of Example 11-15, further comprising: forming a third composition of bonding agent material, wherein the bonding agent material is formed along the perimeter of the ISFET die.

Example 17 includes a pH sensor comprising: a substrate; an ion sensitive field effect transistor (ISFET) die comprising an ion sensing part that responds to pH, wherein the ISFET die is bonded to the substrate; and one or more linear strips of a first frit material disposed between the ISFET die and the substrate, wherein the one or more linear stripes are all disposed in the same direction.

Example 18 includes the pH sensor of Example 17, further comprising: one or more linear stripes of a second frit material disposed between the substrate and the ISFET die, wherein the one or more linear strips of the second frit material are disposed in a direction orthogonal to the direction of one or more linear stripes of the said first frit material; and wherein the coefficient of thermal expansion (CTE) of the second frit material is different from the CTE of the first frit material such that at different temperatures the two materials induce force on the die in different directions to produce biaxial loading conditions.

Example 19 includes the pH sensor of Example 17 or Example 18, further comprising: a third frit material, wherein the frit material is formed along the perimeter of the said ISFET die.

Example 20 includes the pH sensor of Example 19, wherein the CTE of the third frit material is the same as the CTE of the first frit material.

What is claimed is:
1. A pH sensor comprising:
   a substrate;
   an ion sensitive field effect transistor (ISFET) die including an ion sensing part that responds to pH, wherein the ISFET die is bonded to the substrate; wherein the ion sensing part of the ISFET die is configured to be exposed to a medium, and wherein the ion sensing part outputs a signal related to a pH level of the medium; and
   a plurality of strips of at least one composition of a bonding agent material disposed in a first pattern between the substrate and the ISFET die, wherein the plurality of strips induce a counteracting force in a direction that counteracts at least a portion of environmental forces on the ISFET die during thermal changes, and wherein the counteracting force is configured to maintain the change in piezoresistance of the ISFET die from a drain to a source to less than 0.5%.
2. The pH sensor of claim 1, further comprising:
   one or more strips of a second composition of a bonding agent material disposed between the substrate and the ISFET die in a second pattern, wherein the coefficient of thermal expansion (CTE) of the second composition is different from the CTE of the first composition such that at different temperatures the two materials induce forces on the die in different directions.

3. The pH sensor of claim 2, wherein one or more strips of the second composition of bonding agent material are disposed orthogonally to the plurality of strips of the first composition.

4. The pH sensor of claim 1, further comprising:
an inert material, wherein the inert material supports a portion of the ISFET die and does not exert a force due to CTE on the said portion of the ISFET die.

5. The pH sensor of claim 1, wherein the at least one composition of a bonding agent material comprises a glass frit.

6. The pH sensor of claim 1, wherein the ISFET die is bonded to the substrate by anodic bonding, eutectic bonding, or adhesive bonding.

7. The pH sensor of claim 1, further comprising:
a third composition of a bonding agent material, wherein the third composition of bonding agent material is disposed along the perimeter of the said ISFET die.

8. The pH sensor of claim 7, wherein the third composition of a bonding agent material is the same as the at least one composition of a bonding agent material.

9. The pH sensor of claim 1, wherein the substrate comprises a base substrate and a cap formed over the base substrate, the pH sensor further comprising:
a protective layer formed over at least a portion of an outer surface of the ISFET die and at least a portion of the cap substrate;
a cover member mechanically coupled to the protective layer, wherein the cover member houses the ISFET die and the substrate, and wherein the cover member defines an opening proximate to the ion sensing part;
a header, wherein the substrate is mounted to the header;
a reference electrode that provides a reference voltage; and
at least one electric pin coupled to the ISFET die via a wire.

10. The pH sensor of claim 1, wherein the at least one composition of bonding agent material comprises an epoxy with filler material.

11. A pH sensor comprising:
a substrate;
an ion sensitive field effect transistor (ISFET) die comprising an ion sensing part that responds to pH, wherein the ISFET die is bonded to the substrate; and
a plurality of linear strips of a first frit material disposed between the ISFET die and the substrate, wherein the plurality of strips are all disposed in the same direction, wherein the plurality of strips induce a counteracting force in a direction that counteracts at least a portion of environmental forces on the ISFET die during thermal changes, and wherein the counteracting force is configured to maintain the change in piezoresistance of the ISFET die from a drain to a source to less than 0.5%.

12. The pH sensor of claim 11, further comprising:
one or more linear stripes of a second frit material disposed between the substrate and the ISFET die,
wherein the one or more linear strips of the second frit material are disposed in a direction orthogonal to the direction of a plurality of linear strips of the said first frit material; and
wherein the coefficient of thermal expansion (CTE) of the second frit material is different from the CTE of the first frit material such that at different temperatures the two materials induce force on the die in different directions to produce biaxial loading conditions.

13. The pH sensor of claim 11, further comprising:
a third frit material, wherein the frit material is formed along the perimeter of the said ISFET die.

14. The pH sensor of claim 13, wherein the CTE of the third frit material is the same as the CTE of the first frit material.

* * * * *